(12) United States Patent
Chao

(10) Patent No.: US 8,065,781 B2
(45) Date of Patent: Nov. 29, 2011

(54) ADJUSTABLE TOURNIQUET

(75) Inventor: Chia-Chang Chao, Taipei (TW)

(73) Assignee: Huntex Corporation, Taipei (TW)

( * ) Notice: Subject to any disclaimer, the term of this patent is extended or adjusted under 35 U.S.C. 154(b) by 464 days.

(21) Appl. No.: 12/325,728

(22) Filed: Dec. 1, 2008

(65) Prior Publication Data
US 2010/0137900 A1    Jun. 3, 2010

(51) Int. Cl.
*A61B 17/00* (2006.01)
(52) U.S. Cl. .................. 24/70 ST; 24/68 B; 24/265 BC; 24/265 CD; 606/203; 254/365; 254/217
(58) Field of Classification Search .................. 606/203, 606/202; 24/69 R, 68 R, 69 ST, 70 ST, 69 CT, 24/68 CD, 68 B, 68 E, 265 BC, 265 CD; 254/217, 223, 365, 391, 411
See application file for complete search history.

(56) References Cited

U.S. PATENT DOCUMENTS

| | | | | |
|---|---|---|---|---|
| 4,155,537 A | * | 5/1979 | Bronson et al. ............ | 242/388.3 |
| 4,199,182 A | * | 4/1980 | Sunesson ................... | 24/68 CD |
| 4,542,883 A | * | 9/1985 | Rutzki ........................ | 254/217 |
| 6,095,450 A | * | 8/2000 | Jang .......................... | 242/388.5 |
| 6,547,218 B2 | * | 4/2003 | Landy ........................ | 254/217 |
| 6,654,987 B1 | * | 12/2003 | Wu ............................ | 24/68 CD |
| 6,960,223 B1 | * | 11/2005 | Ambach ..................... | 606/203 |
| 7,207,089 B2 | * | 4/2007 | Hanson ..................... | 24/68 CD |
| 7,510,168 B1 | * | 3/2009 | Lin ............................ | 254/218 |
| 7,712,192 B2 | * | 5/2010 | Lin et al. ................... | 24/70 ST |
| 7,743,473 B2 | * | 6/2010 | Lin et al. ................... | 24/71 ST |

FOREIGN PATENT DOCUMENTS

| TW | M263082 | 5/2005 |
|---|---|---|
| TW | M318404 | 9/2007 |

\* cited by examiner

*Primary Examiner* — Robert Sandy
*Assistant Examiner* — Rowland D Do
(74) *Attorney, Agent, or Firm* — Muncy, Geissler, Olds & Lowe, PLLC

(57) ABSTRACT

An adjustable tourniquet includes a first component, a second component, a third component and a band. Two ends of the first component respectively have an axle for fixing the band and a buckling trough with an engaging element, wherein two ends of the axle respectively have a ratchet. The first and second components respectively have a rejecting element and a driving element to stop the ratchet. The axle is clamped by an axial cover, and two ends of the axle are respectively connected with a connecting axle for penetrating the second component. Furthermore, the ratchet includes an inner and an outer ratchet surfaces respectively for butting the rejecting element and the driving element, and the teeth of the inner and outer ratchet surfaces are respectively bent toward the same direction and the arrangement of the inner and outer ratchet surfaces are perpendicular to each other.

4 Claims, 17 Drawing Sheets

ADJUSTABLE TOURNIQUET

FIELD OF THE INVENTION

The present invention is related to a tourniquet, and more particularly to a tourniquet which is capable of achieving rapid engagement and slight adjustment.

BACKGROUND OF THE INVENTION

When accident happens, the most common situation might be the human body get hurt and some cuts or wounds are made with blood, so that stopping bleeding is the initial action of the first aid.

Usually, the slight trauma, like cut and wound, caused in daily life, is bleeding caused in the blood capillary or slight vein. The most common way to stop bleeding is to apply direct pressure on the bleed, and to band the wound then, so that the blood on the wound can have a spontaneous clot and callus. Moreover, when the trauma is more serious, such as injury of vein or slight artery, the bleeding volume becomes more and is more difficult to clot, so that in addition to direct pressure, lifting up the injured limb or applying point pressure for stopping bleeding have been used simultaneously. For the most severe situation, for example, the limb is broken to cause a large amount of blood loss, the most important thing is to keep alive, so that the emergent method is to use tourniquet to stop bleeding. But, as known, applying tourniquet might easily kill the tissue, so that it should be the last resort to use.

The principle of tourniquet is to constrict or compress the vicinity of the bleeding portion for stopping blood loss. Since it is usually used in the emergency, the essential conditions of a well-designed tourniquet should be easy to arrange with capabilities of providing sufficient strength, rapid fixing and easy to disengage. There are many types of the tourniquets. One of them is TWP No. M263082, entitled "Improved structure of tourniquet", including a release buckle with a tongue and an engaging portion which are connected by a band. When using this tourniquet, the band is applied circumferentially upon the bleeding portion, and the tongue and the engaging portion are engaged together for fixing the band. Then, through a circling structure in the tongue, the band can be tightened by pulling so as to stop bleeding. However, this application could not provide a strong pressure and might easily become loose owing to an external touch to contact the upright tourniquet. Another example is TWP No. M318404, entitled "Adjustable tourniquet", in which two ends of a band are respectively connected to a first housing and a third housing, which are buckled together to loop the band, and through a structure in the third housing, the band can be tightened by applying force. Further, it is characterized in that a second housing is included, wherein an axle of the second housing is passed through a hollow axial tube of the first housing, and the first and the second housings have a rejecting element, plural ratchets and a driving element, so that when the second housing moves by pivoting about the axial tube, through the orientation mechanism of the ratchets, the band can have a slight adjustment. However, when applying this structure, the user might easily touch the sliding portion so as to move the driving element, thereby loosing the tightening strength. Beside, the structure of hollow axial tube cooperating with the axle is complicated, and the overlapped rejecting element and the driving element form a thicker structure which increases the collision possibility, and thus, the loosing possibility would be present.

SUMMARY OF THE INVENTION

The present invention provides an adjustable tourniquet which simplifies the axial structure for rolling the band and improves the structure of ratchet for thinning, so as to solve the problems described in the prior arts.

For achieving the object described above, the present invention includes a first component, a second component, a third component and a band for encircling human body. One end of the first component has an axle for fixing the band and the other end has a buckling trough with at least an engaging element, wherein two ends of the axle respectively have a ratchet, and the first component at least has a rejecting element for resisting the ratchet. The second component which is covered on the first component at least includes a driving element to stop the ratchet. The third component has a buckling element at one end thereof for coupling with the engaging element, and the other end is an opening with a pressing shaft for fixing the band. And, the engaging element, the rejecting element and the driving element all have an elastic element for providing a recovering strength. The present invention is characterized in that the axle is a solid axle formed by a semicircular axle being clamped by an axial cover, and two ends of the axle are respectively connected with a connecting axle for penetrating the second component, so that the second component is capable of having a movement relative to the first component by pivoting about the axle, wherein the ratchet includes an inner ratchet surface butted by the rejecting element, and an outer ratchet surface butted by the driving element, and the teeth of the inner and outer ratchet surfaces are respectively bent toward the same direction and the arrangement of the inner and outer ratchet surfaces are perpendicular to each other.

Through the structure described above, the present invention is advantageous that:

1. The axle of the present invention is a solid axle formed by a semicircular axle being clamped by an axial cover, so that the assembly method is simple and the simplified parts make the production easier and lowers down the manufacturing cost.

2. The ratchet of the present invention includes the inner and the outer ratchet surfaces, so that the rejecting element and the driving element can be arranged in parallel, thereby reducing the thickness of the adjustable tourniquet, and thus, diminishing the collision possibility.

BRIEF DESCRIPTION OF THE DRAWINGS

The foregoing aspects and many of the attendant advantages of this invention will be more readily appreciated as the same becomes better understood by reference to the following detailed description, when taken in conjunction with the accompanying drawings, wherein.

DESCRIPTION OF THE PREFERRED EMBODIMENT

Figure 1:
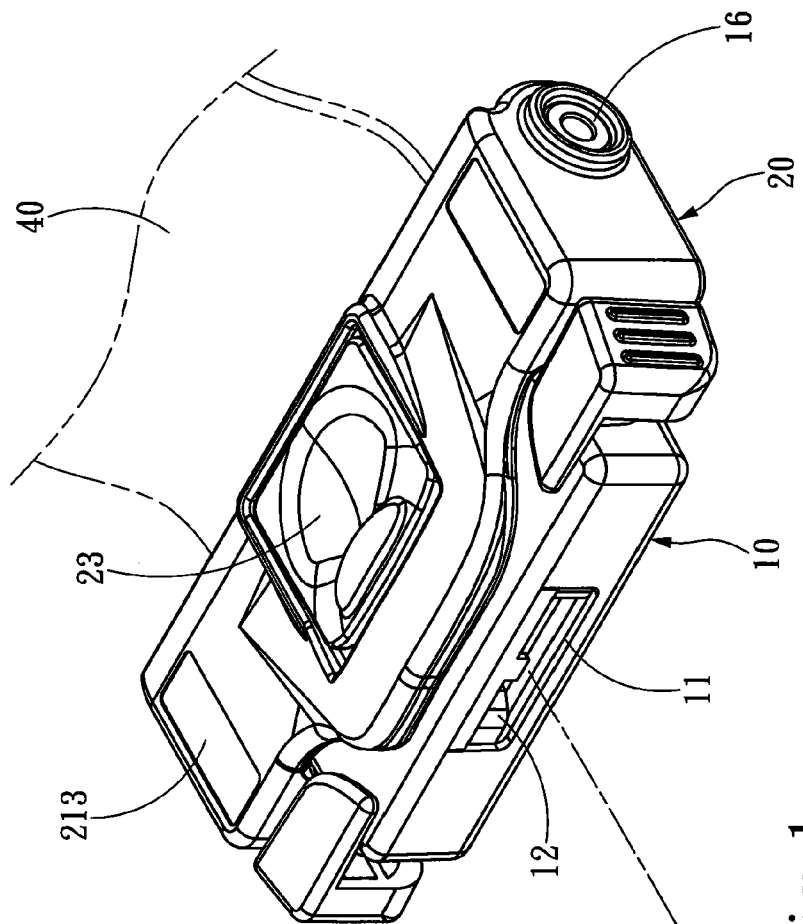
FIG. 1 is a drawing showing the appearance of the present invention.
Figure 1:
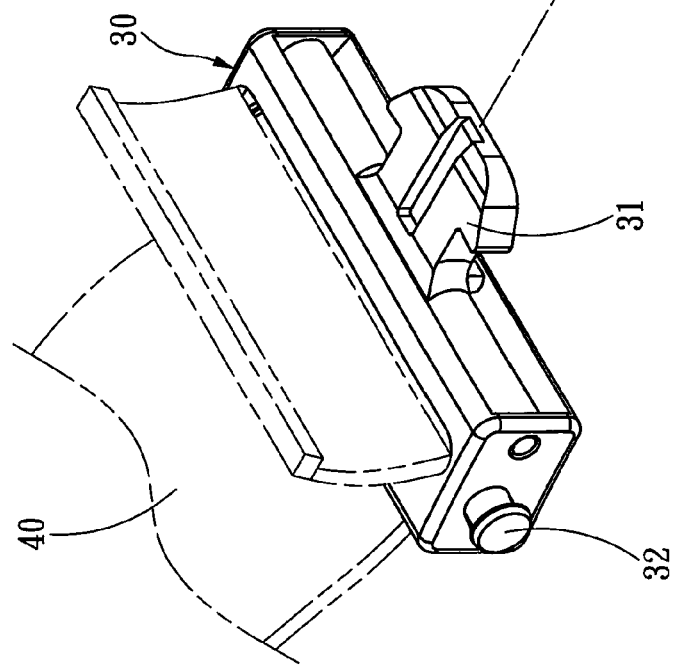

Please refer FIG. 1 to FIG. 4. The present invention includes a first component 10, a second component 20, a third component 30 and a band 40 for encircling human body. One end of the first component 10 has an axle 13 for fixing the band 40 and the other end has a buckling trough 11 with at least an engaging element 12, wherein two ends of the axle 13 respectively have a ratchet 14. And, the first component 10 at least has a rejecting element 15 for resisting the ratchet 14. As shown, the axle 13 and the rejecting elements 15 at the two ends thereof are integrally formed. However, the rejecting elements 15 also can be formed as independent elements. Moreover, the second component 20 which is covered on the first component 10 at least includes a driving element 21 to stop the ratchet 14, wherein the driving element 21, as shown, can be accommodated in an accommodating trough 212 on the second component 20 and positioned and sealed by a trough cover 213. Furthermore, the third component 30 has a buckling element 31 at one end thereof for coupling with the engaging element 12, and the other end is an opening with a pressing shaft 32 for fixing the band 40. The engaging element 12, the rejecting element 15 and the driving element 21 all have an elastic element 50 for providing a recovering strength. The whole structure is characterized in that the axle 13 is a solid axle formed by a semicircular axle 131 being clamped by an axial cover 132, and two ends of the axle are respectively connected with a connecting axle 16 for penetrating the second component 20, so that the second component 20 can have a movement relative to the first component 10 by pivoting about the axle 13. Besides, the ratchet 14 includes an inner ratchet surface 141 butted by the rejecting element 15, and an outer ratchet surface 142 butted by the driving element 21. Here, the teeth of the inner and outer ratchet surfaces 141, 142 are respectively bent toward the same direction and the arrangement of the inner and outer ratchet surfaces 141, 142 are perpendicular to each other. In addition, for restricting a loosing capability of the rolling of the axle to be presented only when the first component 10 and the second component 20 are overlapped, so as to prevent the error touch from influencing the operation stability of the adjustable tourniquet, the second component 20 further includes a through hole 22, and the through hole 22 has a sliding piece 23 mounted thereon. When the first and the second components 10, 20 are overlapped, the movement of the sliding piece 23 can drive the movement of the rejecting element 15 for loosing the ratchet 14, and the driving 21 further has a bulge 211 mounted thereon and the first component 10 has a resisting portion 152 mounted thereon, so that when the first and the second components 10, 20 are overlapped, the bulge 211 will be butted by the resisting portion 152 to move and drive the driving element 21 to leave the ratchet 14. In this embodiment, the resisting portion 152 is located at the outer edge of the rejecting element 15. The movement relationship among the sliding piece 23, the driving element 21 and the rejecting element 15 makes the present invention more effective.

Figure 5:
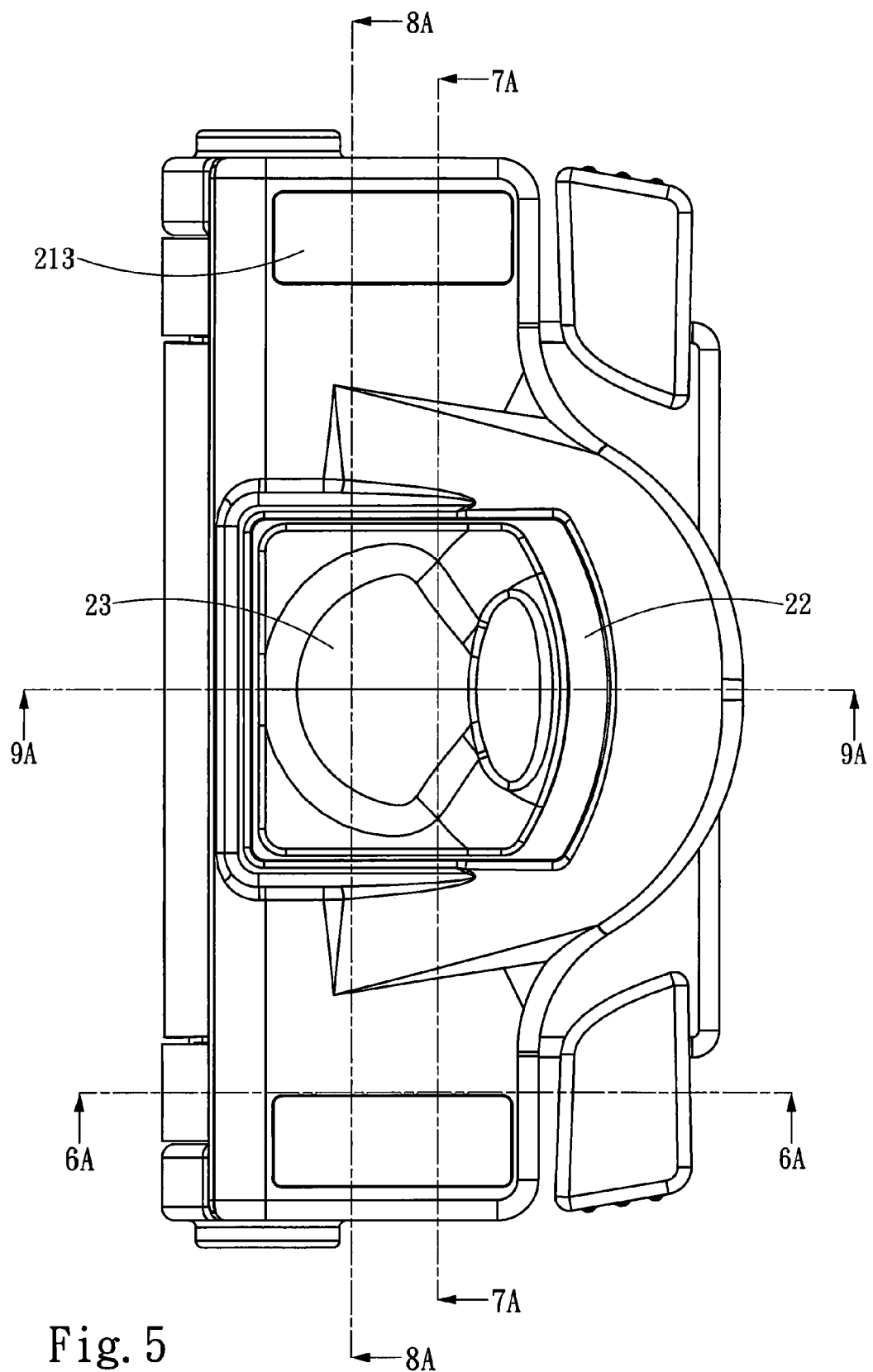
FIG. 5 is a vertical view showing the first component of the present invention.

According to the structure described above, through the rejecting element 15 of the first component 10 and the driving element 21 of the second component 20 simultaneously butt the inner and the outer ratchet surfaces 141, 142, when the second component 20 have a movement by pivoting about the axle 13, the driving element 21 can drive the ratchet 14, so as to turn the axle 13 in one direction, thereby rolling up and tightening the band 40. The details are shown in FIG. 5 and refer to the following descriptions.

Figure 6A:
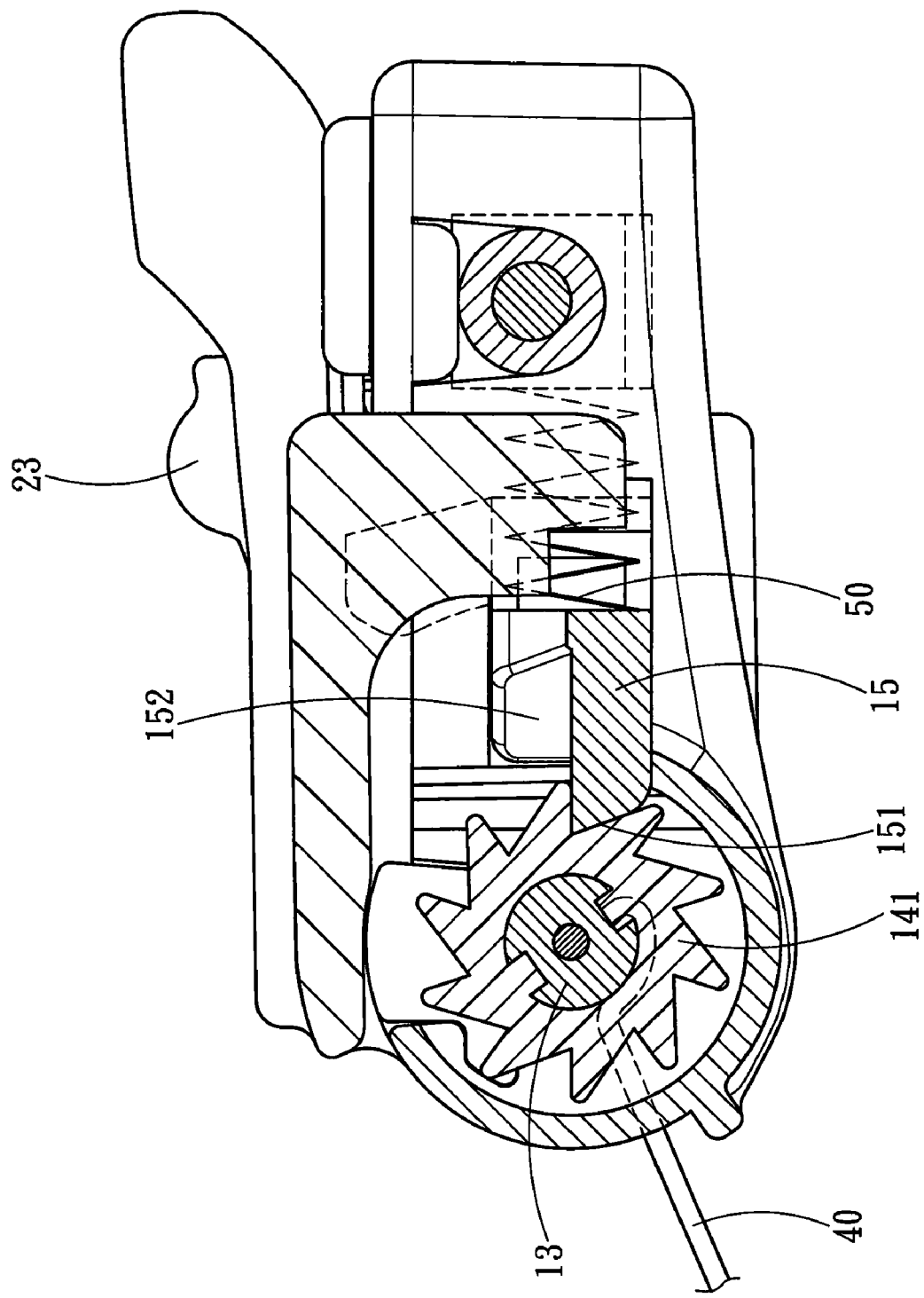
FIG. 6A to FIG. 6C are sectional views of line 6A-6A showing actions of the present invention.
Figure 7A:
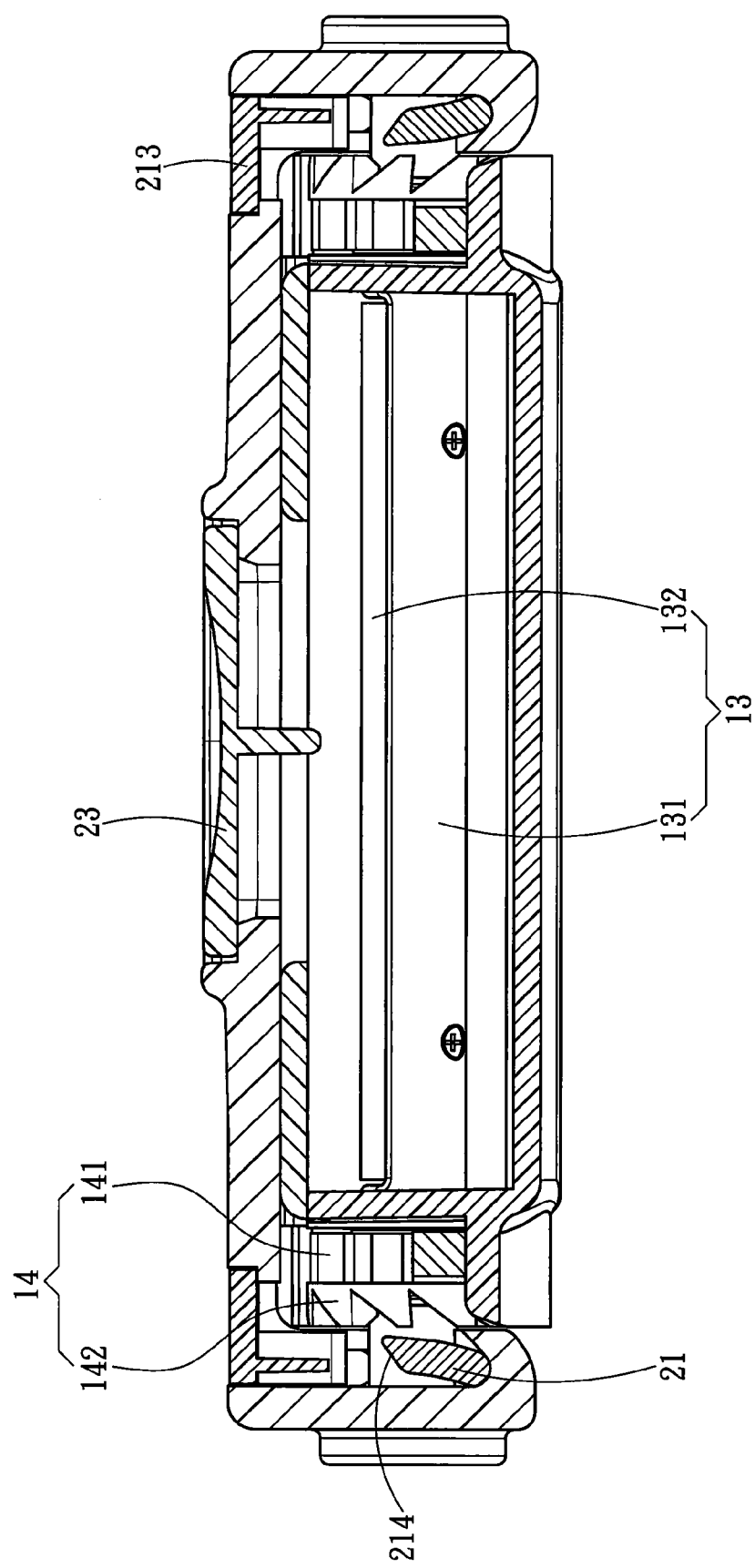
FIG. 7A to FIG. 7C are sectional views of line 7A-7A showing actions of the present invention.
Figure 8A:
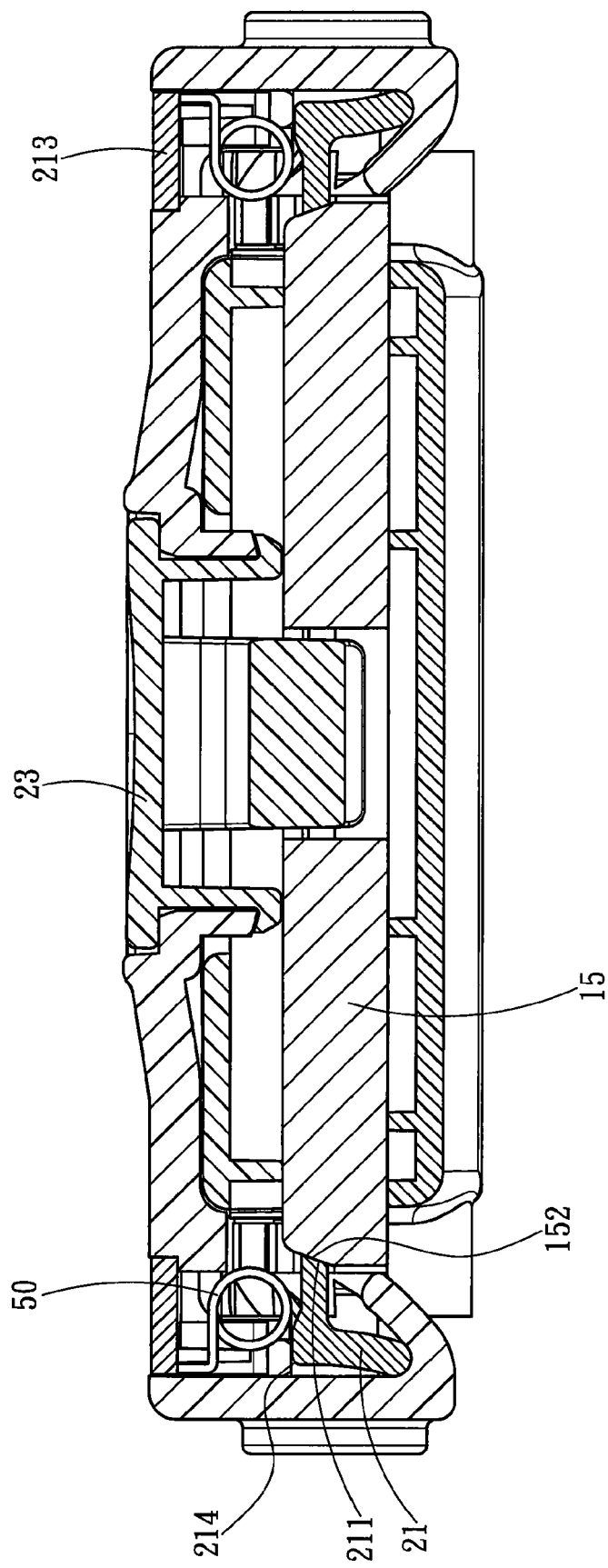
FIG. 8A to FIG. 8C are sectional views of line 8A-8A showing actions of the present invention.

First, please refer to FIG. 6A, FIG. 7A and FIG. 8A. As beginning, the first component 10 is overlapped on the second component 20, and the rejecting element 15 is butted by the inner ratchet surface 141, wherein the rejecting element 15 has an inclined surface 151 at the end to butt the inner ratchet surface 141, thereby the rejecting element 15 can match to the bending direction of the plural teeth of the inner ratchet surface 141, and at the same time, the bulge 211 of the driving element 21 is blocked by the resisting portion 152, so as to deviate from the outer ratchet surface 142.

Figure 6B:
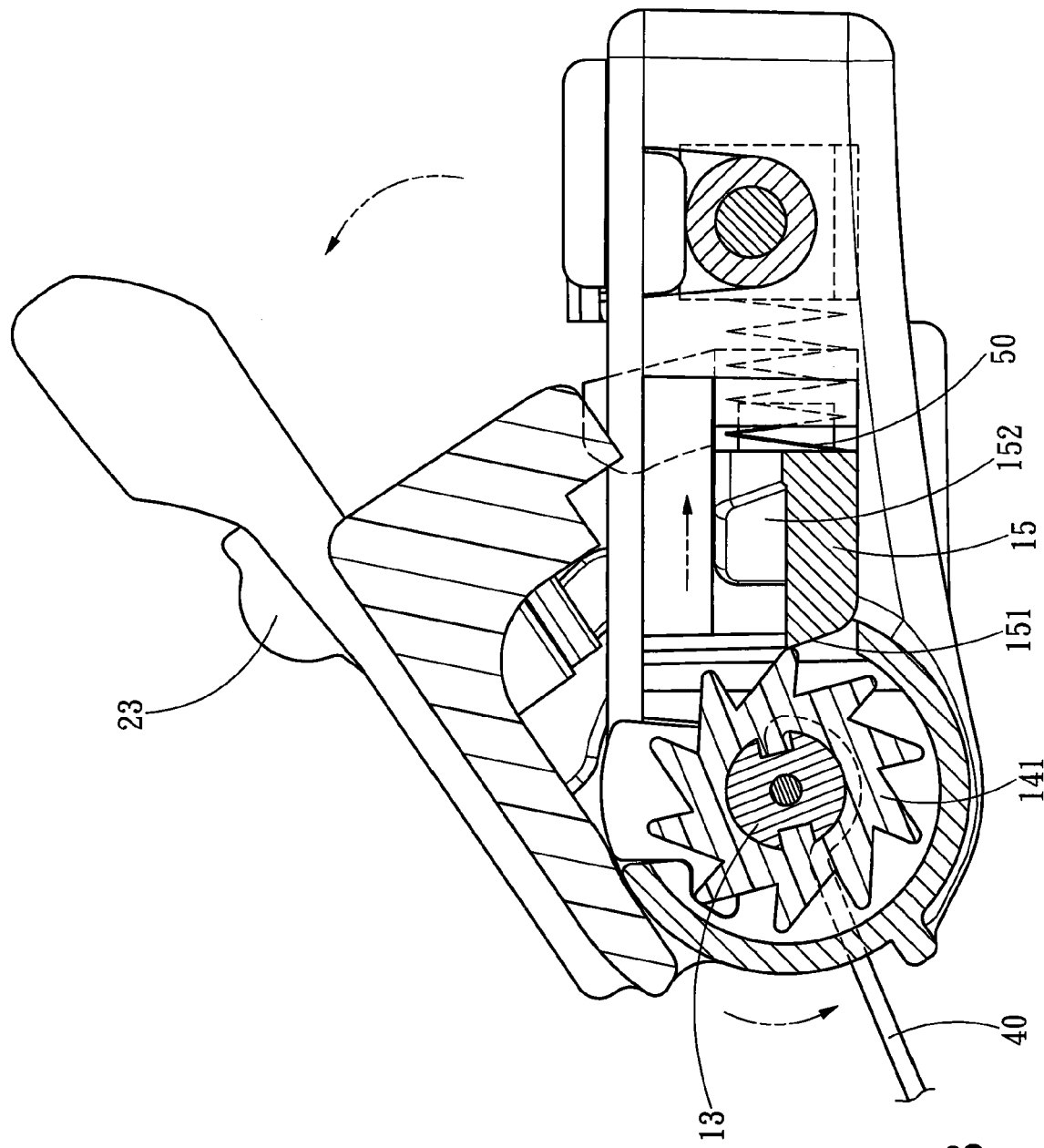
Figure 7B:
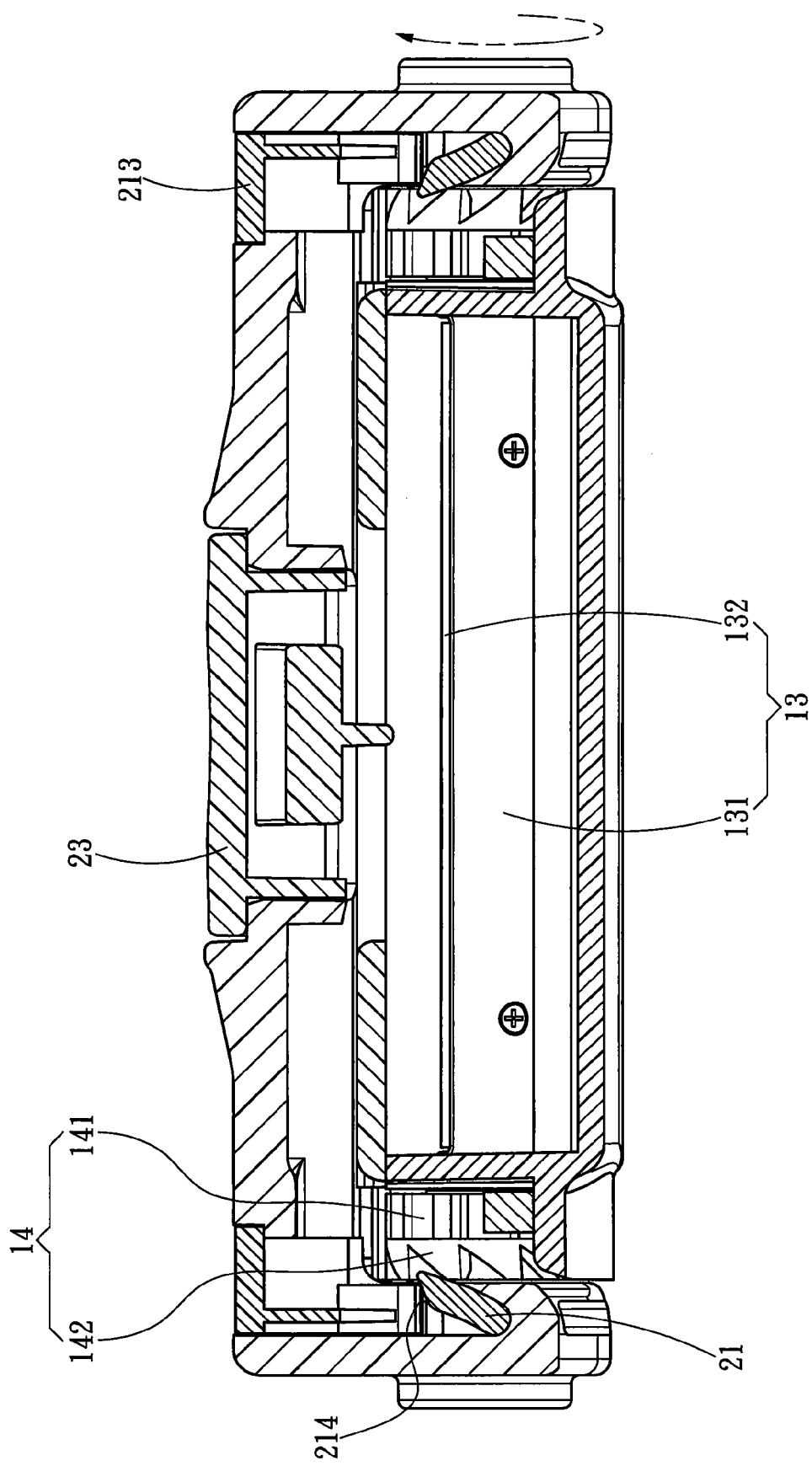
Figure 8B:
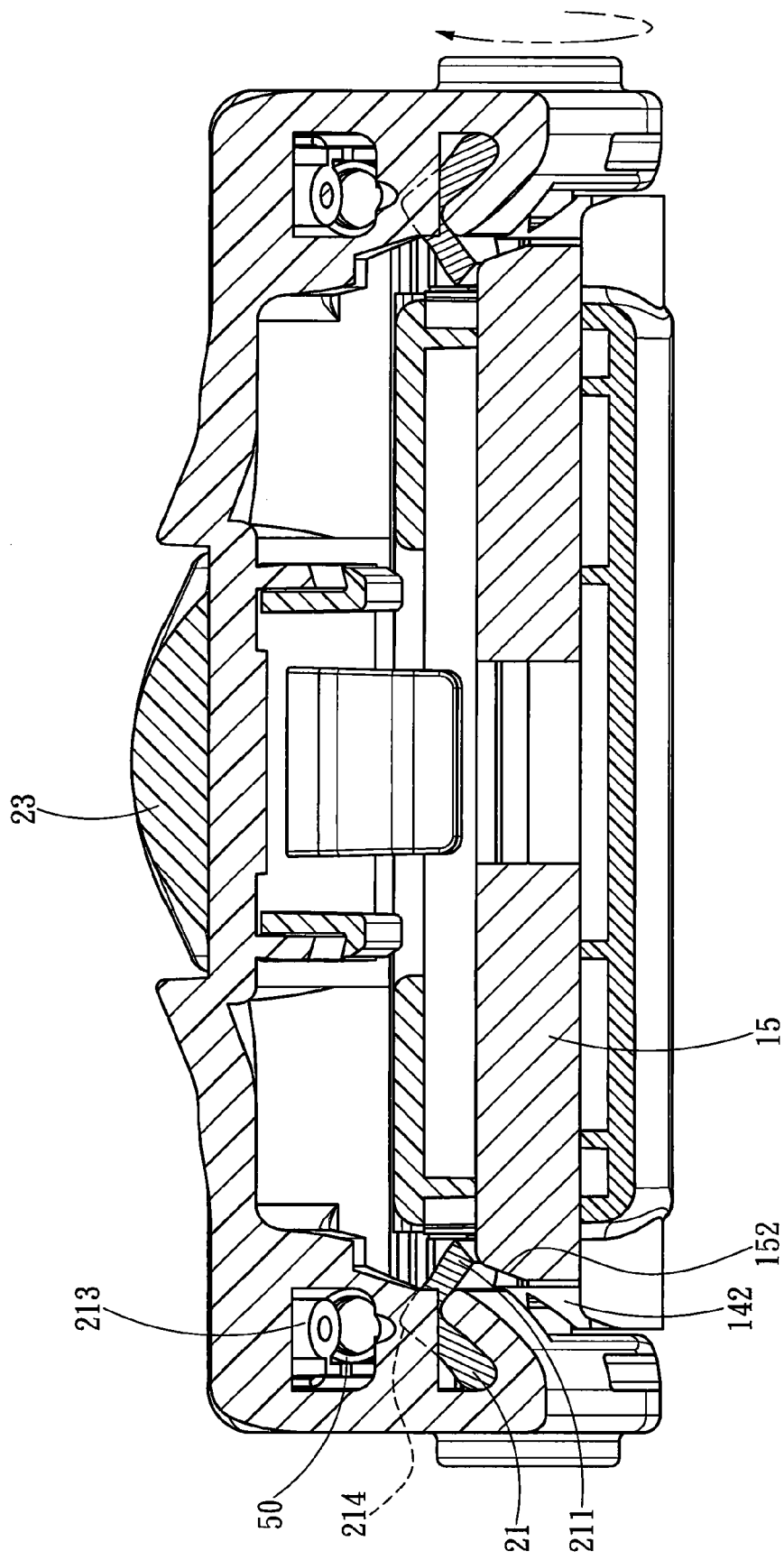

Then, when trying to roll up the band 40, the second component 20 can be pushed to have a movement relative to the first component 10 by pivoting about the axle 13, as shown in FIG. 6B, FIG. 7B and FIG. 8B. At this time, the bulge 211 of the driving element 21 deviates from the resisting portion 152 and goes back to the position to butt the outer ratchet surface 142 by the recovering strength provided by the elastic element 50, wherein the driving element 21 has an inclined surface 214 at the end to butt the outer ratchet surface 142, thereby the driving element 21 can match to the bending direction of the plural teeth of the outer ratchet surface 142 and thus drive the ratchet 14 to turn, and at the same time, the rejecting element 15 butted by the inner ratchet surface 141 is turned owing to the ratchet 14. Here, since the inclined surface 151 is pushed by the teeth of the inner ratchet surface 141 along the bending direction and the elastic element 50 provides the space for the rejecting element 15 to slightly move backward, the turning of the ratchet 14 will not be influenced.

Figure 6C:
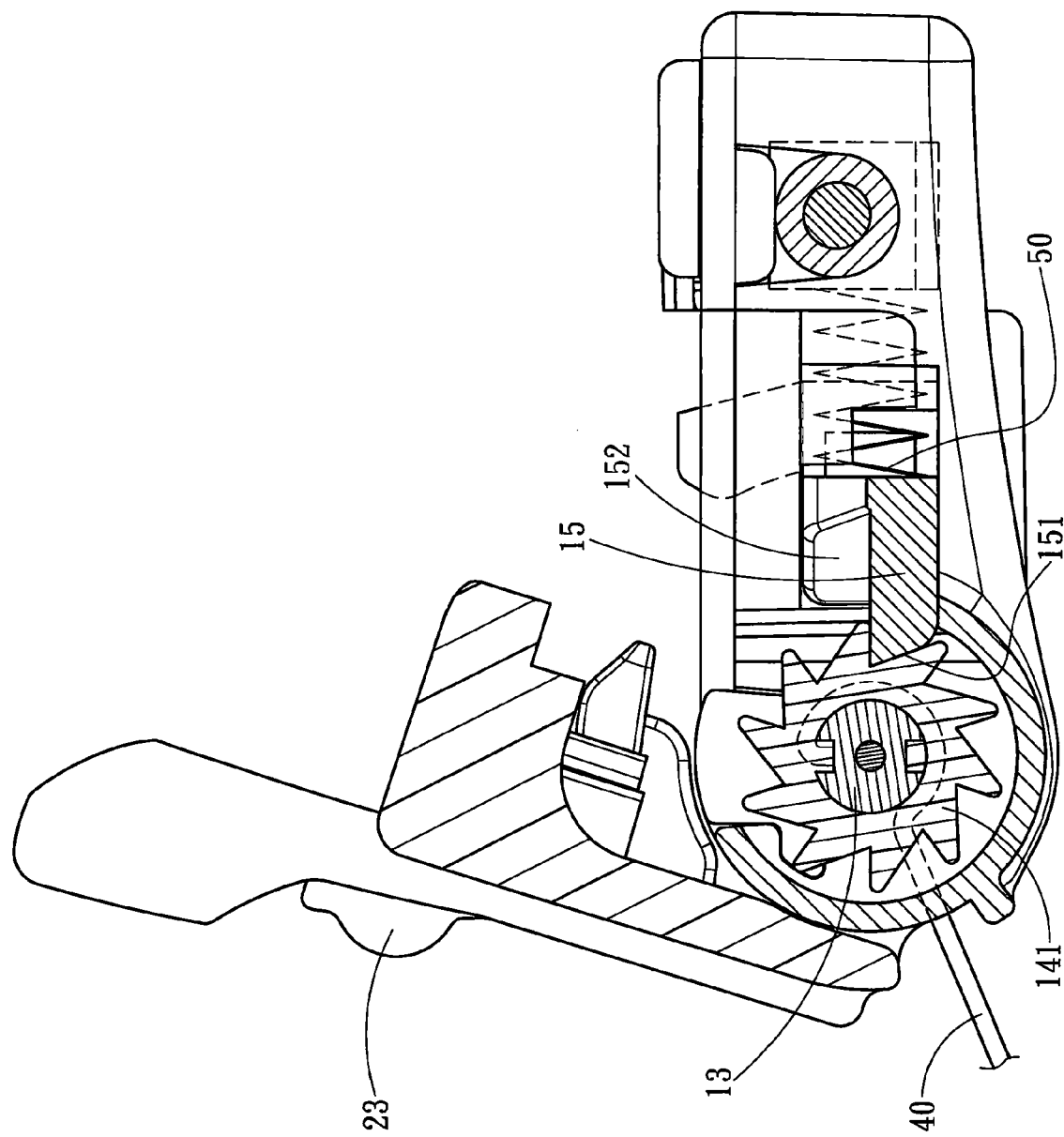
Figure 7C:
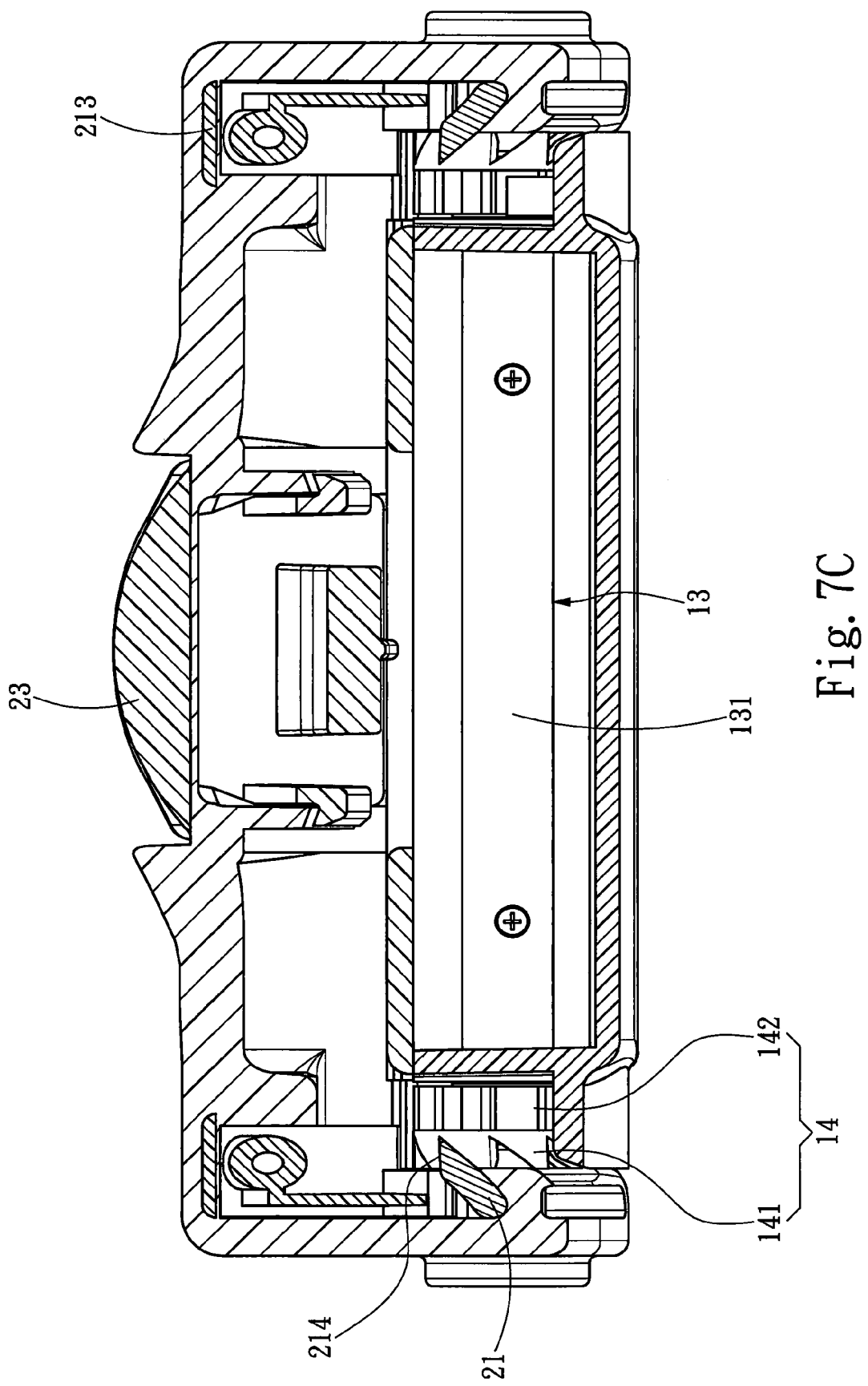
Figure 8C:
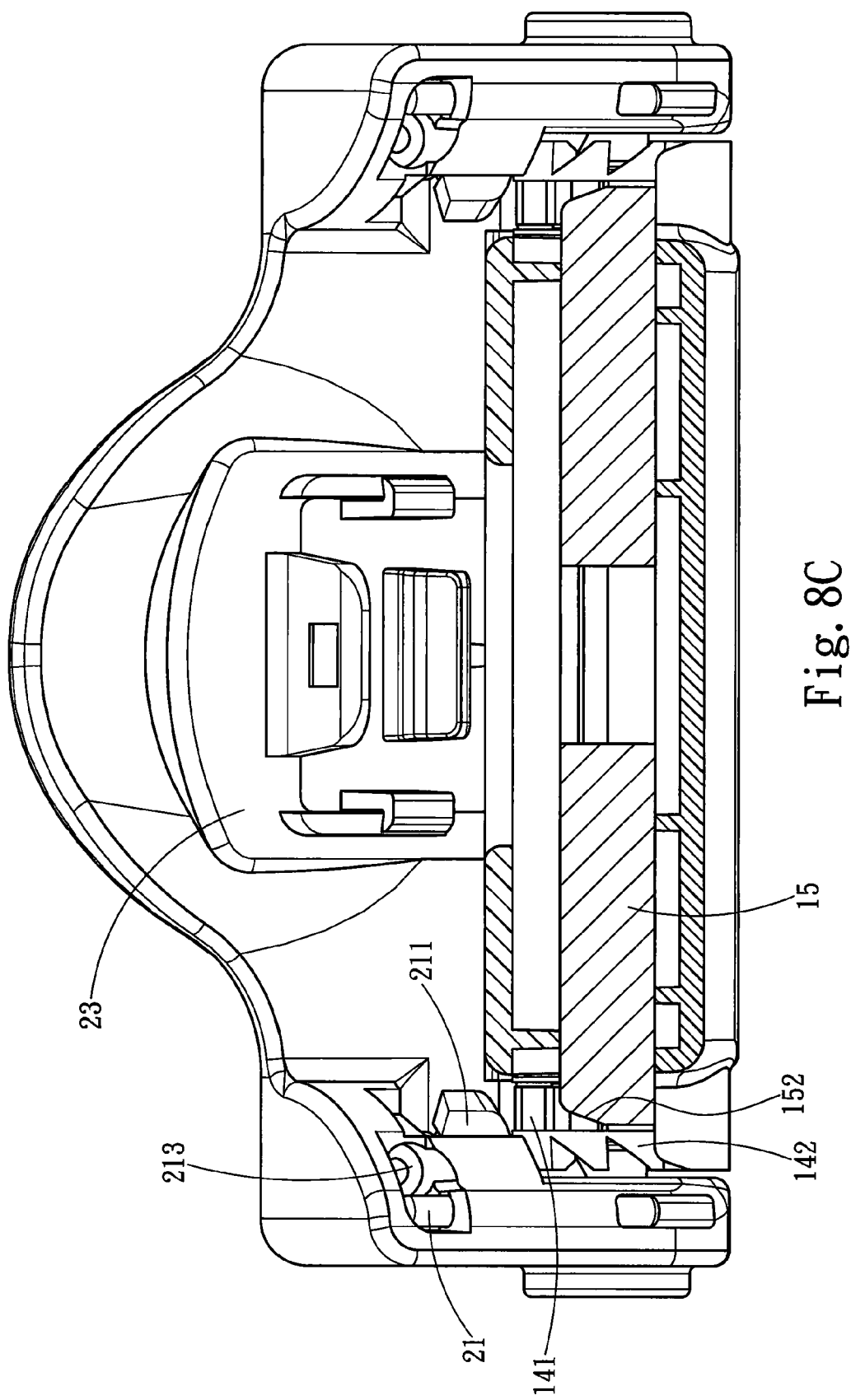

Finally, please refer to FIG. 6C, FIG. 7C and FIG. 8C which show the larger movement of the second component 20 by pivoting about the axle 13. At this time, because the moving direction of the driving element 21 is reverse to the bending direction of the teeth of the outer ratchet surface 142, the driving element 21 will butt and drive the ratchet 14 to turn, and simultaneously, since the moving direction of the rejecting element 15 is identical to the bending direction of the teeth of the inner ratchet surface 141 and thus the inclined surface 151 is pushed backward, the turning of the ratchet 14 will not be influenced. On the other hand, when the second component 20 is pushed back to the position overlapping the first component 10, since the moving direction of the rejecting element 15 is reverse to the bending direction of the teeth of the inner ratchet surface 141, the inner ratchet surface 141 is resisted by the rejecting element 15, so that the ratchet 14 and the axle 13 will not be turned back owing to the recovery of the second component 20. At the same time, because the moving direction of the driving element 21 is identical to the bending direction of the teeth of the outer ratchet surface 142 and the inclined surface 214 can be moved backward owing to the elastic element 50, the ratchet 14 will not be influenced. Through the actions described above, when the second component 20 has a recovering movement relative to the first component by taking the axle 13 as the center axial, the ratchet 14 and the axle 13 can keep in turning in one direction, so as to achieve the purpose of slightly adjusting and tolling to tighten the band 40. Here, the inclined surfaces 151, 214 of the rejecting element 15 and the driving element 21 for butting the ratchet 14 are only examples, and there is no limitation to the shape thereof. They can be arc, circular or other shapes which can push or reversely block the ratchet 14 as moving along or reverse the bending direction of the teeth of the ratchet 14.

Figure 2:
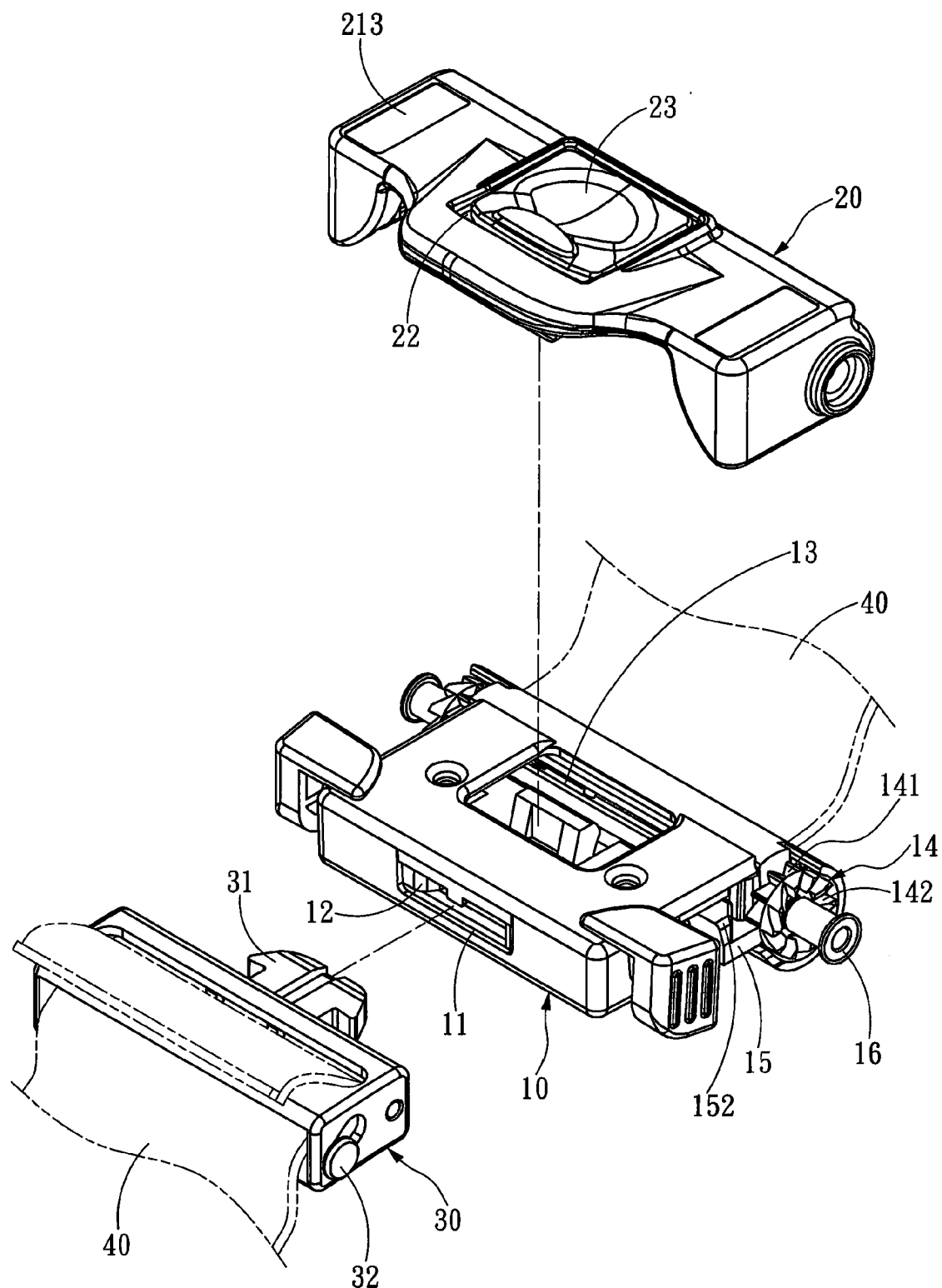
FIG. 2 is a decomposition drawing of the present invention.
Figure 3A:
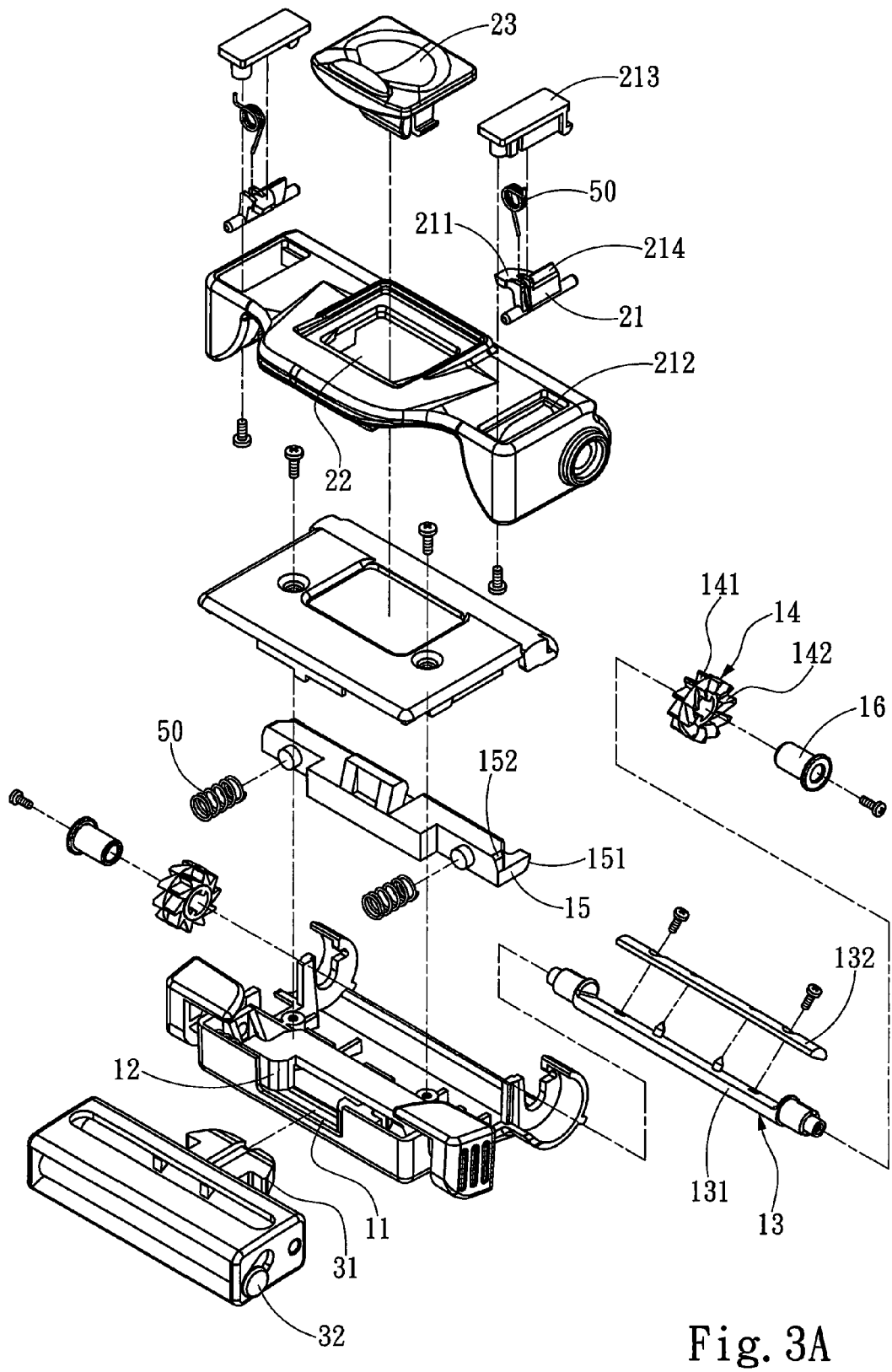
FIG. 3A and FIG. 3B are explosion drawings showing the details of the present invention.
Figure 3B:
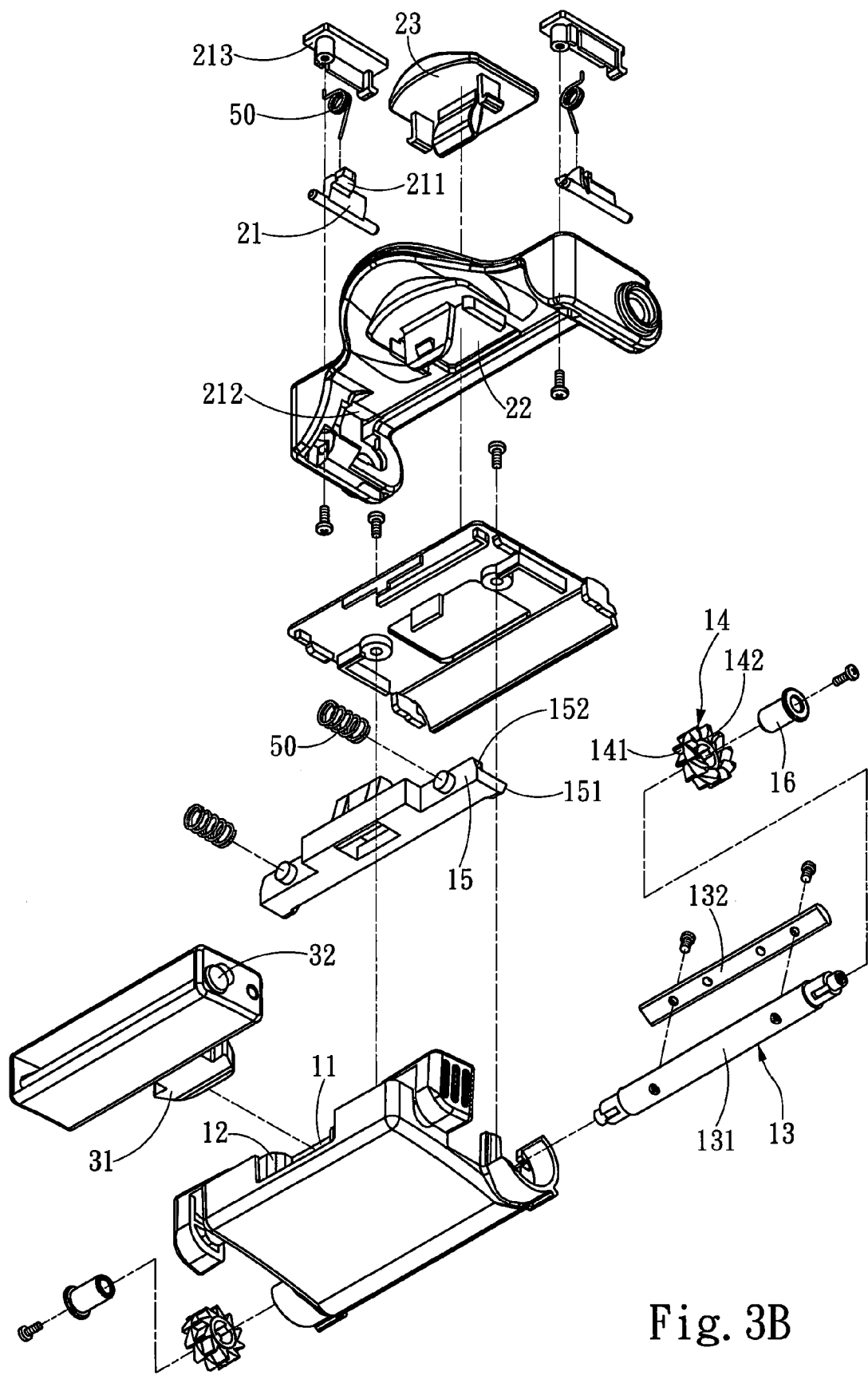
Figure 4:
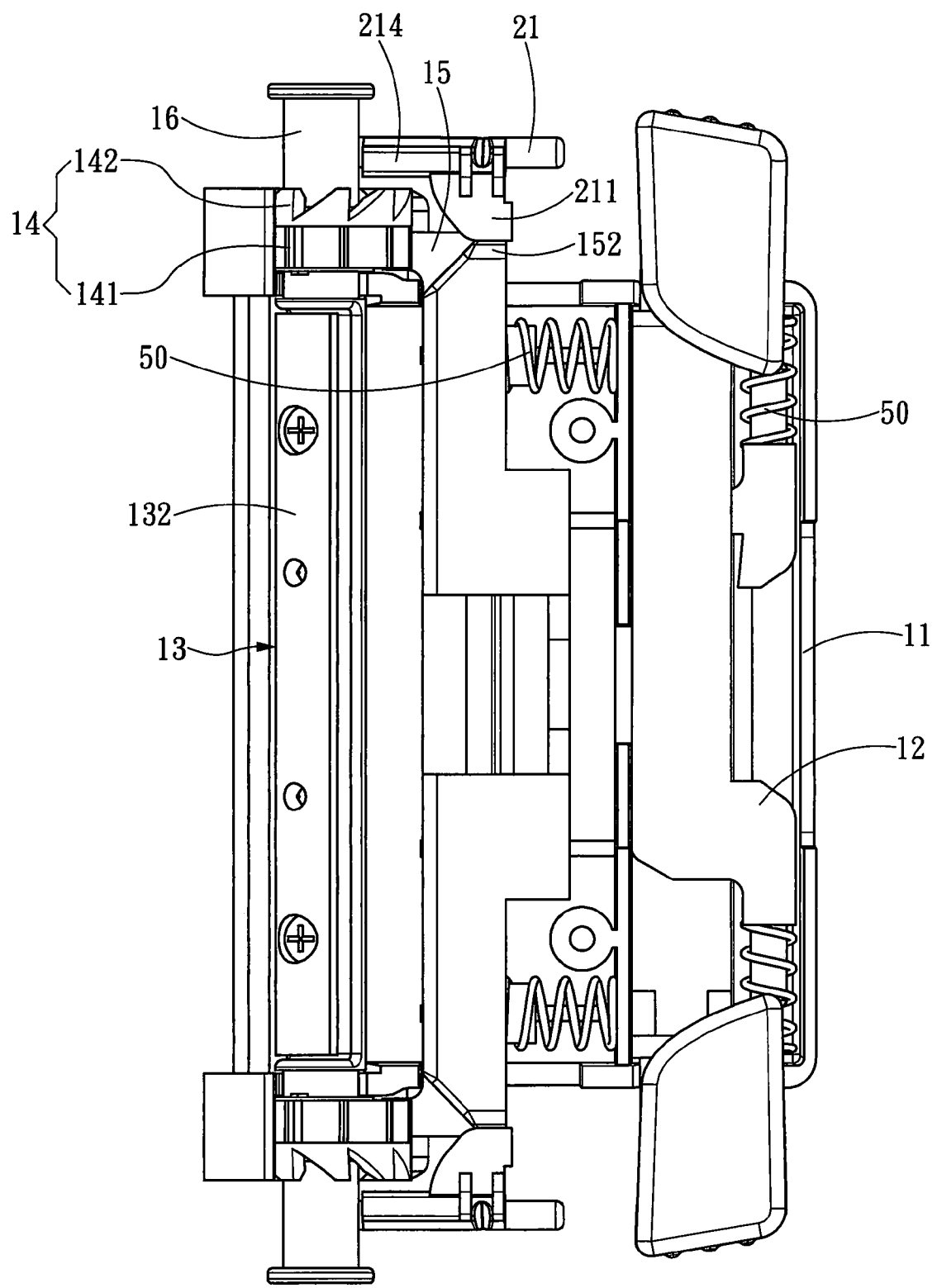
FIG. 4 is a rear view showing the structure of the first component of the present invention.
Figure 9A:
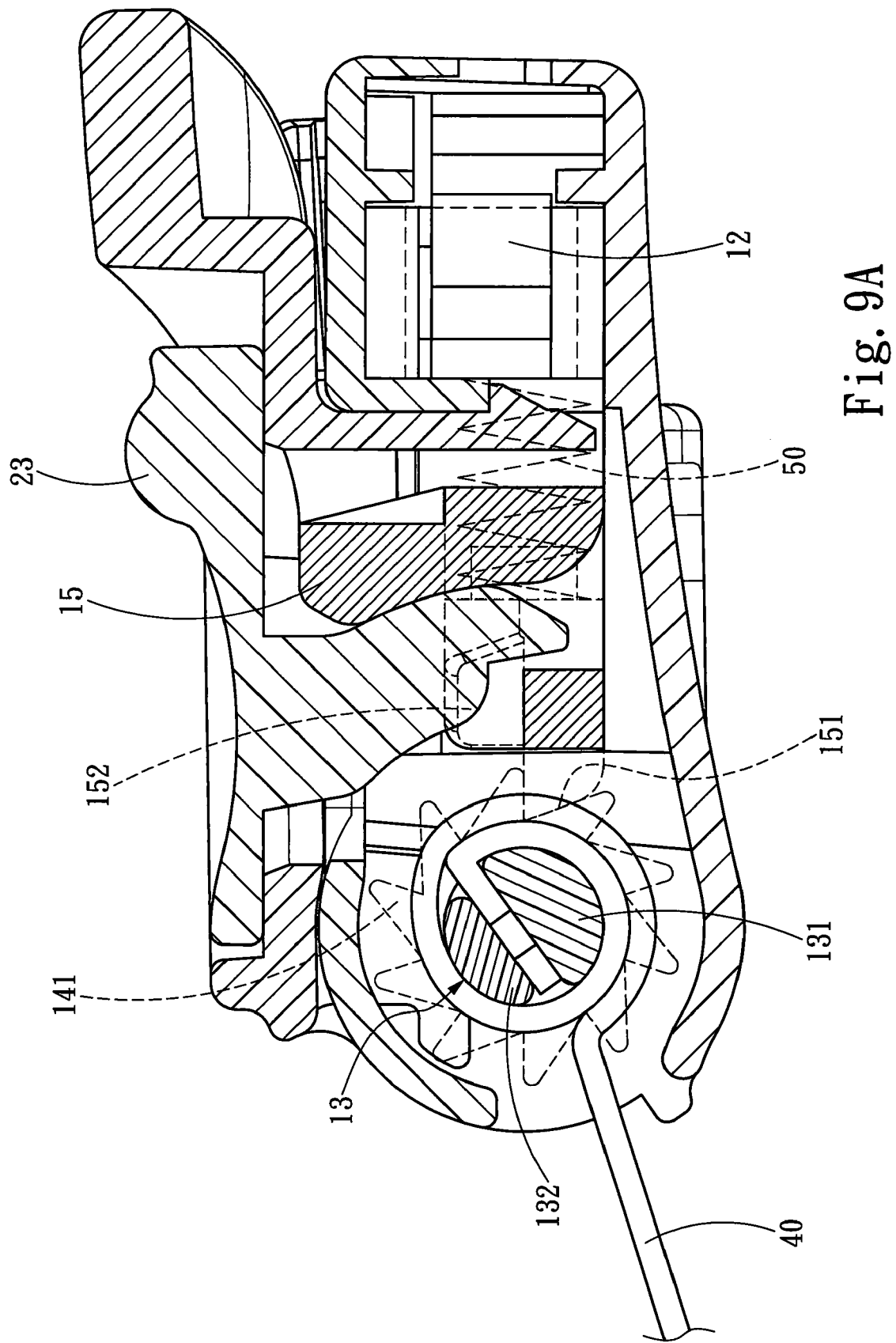
FIG. 9A and FIG. 9B are sectional views of line 9A-9A showing actions of the present invention.
Figure 9B:
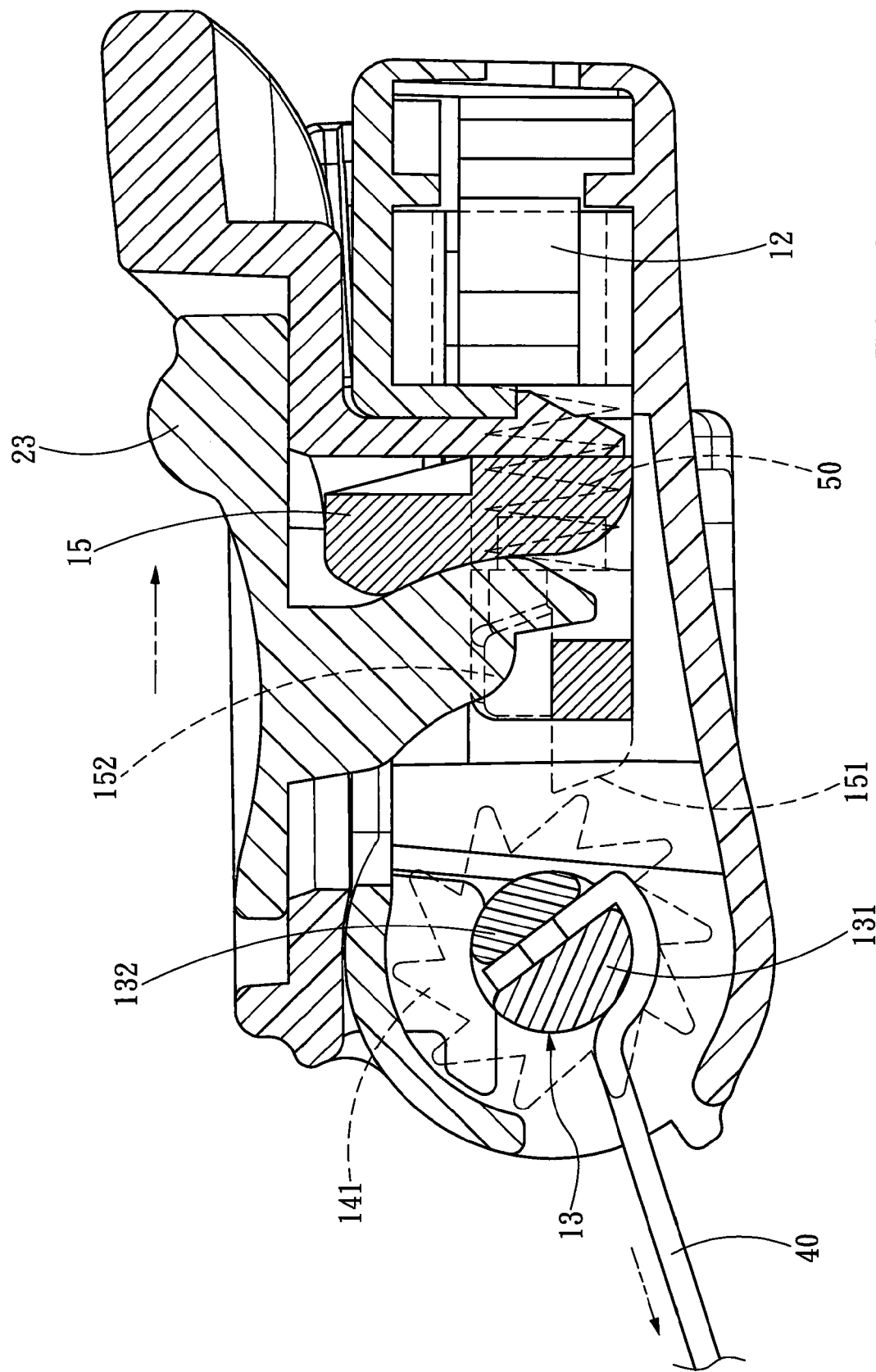

When trying to loose the band 40, as shown in FIG. 2, the buckling element 31 can be moved out from the buckling trough 11 rapidly through adjusting the pressing shaft 32 or pressing the engaging element 12 to make. In practice, without confirming the bleeding situation of the trauma, a rapid loosing of the tourniquet might cause a large amount of bleeding. Therefore, the present invention also provides a structure for slightly loosing, as shown in FIG. 5, FIG. 9A and FIG. 9B, wherein the cooperation of the sliding piece 23 and the rejecting element 15 is used for slightly loosing the band 40. When the first component 10 and the second component 20 are overlapped, the rejecting element 15 stops and positions the ratchet 14 for fixing the ratchet 14. In this embodiment, the first component 10 and the rejecting elements 15 at two ends thereof are integrally formed, and the sliding element 23 butts the rejecting element 15 as the first and the second components 10, 20 are overlapped, so that when the sliding piece 23 is pushed to drive the rejecting element 15 to deviate from the ratchet 14 so as to lose the fixing strength, the band 40 can be loosed. Then, for stopping the loosing of the band 40, it only needs to stop the force applied to the sliding piece 23, so that through the elastic element 50 on the rejecting element 15, the rejecting element 15 can automatically move back and butt the inner ratchet surface 141 again, so as to stop the turning of the ratchet 14. Here, the rejecting element 15 is embodied to be integrally formed with the first component 10, but there is no limitation. The rejecting elements 15 also can be two independent elements respectively mounted at two ends of the first component 10, and in this case, the sliding pieces 23 have to simultaneously butt the independent rejecting elements 15 as the first and the second components are overlapped.

It is to be understood, however, that even though numerous characteristics and advantages of the present invention have been set forth in the foregoing description, together with details of the structure and function of the invention, the disclosure is illustrative only, and changes may be made in detail, especially in matters of shape, size, and arrangement of parts within the principles of the invention to the full extent indicated by the broad general meaning of the terms in which the appended claims are expressed.

What is claimed is:

1. An adjustable tourniquet, comprising a first component, a second component, a third component and a band for encircling a human body, wherein one end of the first component has an axle for fixing the band and the other end has a buckling trough with at least an engaging element, and two ends of the axle respectively have a ratchet, the second component which is covered on the first component at least includes a driving element to stop the ratchet, and the third component has a buckling element at one end thereof for coupling with the engaging element, and the other end is an opening with a pressing shaft for fixing the band, and wherein the engaging element, a rejecting element and the driving element all have an elastic element for providing a recovering strength, characterized in that:

the axle is a solid axle formed by a semicircular axle being clamped by an axial cover, and two ends of the axle are respectively connected with a connecting axle for penetrating the second component, so that the second component is capable of having a movement relative to the first component by pivoting about the axle;

the ratchet includes an inner ratchet surface for butting the rejecting element, and an outer ratchet surface for butting the driving element, and the teeth of the inner and outer ratchet surfaces are respectively bent toward the same direction and arrangement of the inner and outer ratchet surfaces are perpendicular to each other; and through the rejecting element of the first component and the driving element of the second component simultaneously butt the inner and the outer ratchet surfaces, when the second component have a movement by pivoting about the axle, the driving element drives the ratchet, so as to turn the axle in one direction, thereby rolling up and tightening the band.

2. The adjustable tourniquet as claimed in claim 1, wherein the driving has a bulge mounted thereon and the first component has a resisting portion mounted thereon, and when the first and the second components are overlapped, the bulge is butted by the resisting portion to move and drive the driving element to leave the ratchet.

3. The adjustable tourniquet as claimed in claim 2, wherein the second component further includes a through hole with a sliding piece mounted thereon, and when the first and the second components are overlapped, the movement of the sliding piece drives the movement of the rejecting element for loosing the ratchet.

4. The adjustable tourniquet as claimed in claim 1, wherein the second component further includes a through hole with a sliding piece mounted thereon, and when the first and the second components are overlapped, the movement of the sliding piece drives the movement of the rejecting element for loosing the ratchet.

* * * * *